United States Patent [19]

Brois et al.

[11] 4,351,945

[45] Sep. 28, 1982

[54] TWO-PHASE PROCESS FOR THE PREPARATION OF AZOLE AND AZOLINE DISULFIDES

[75] Inventors: Stanley J. Brois, Wantage, England; Antonio Gutierrez, Hamilton Square, N.J.

[73] Assignee: Exxon Research & Engineering Co., Florham Park, N.J.

[21] Appl. No.: 9,741

[22] Filed: Feb. 5, 1979

Related U.S. Application Data

[62] Division of Ser. No. 970,230, Dec. 18, 1978, Pat. No. 4,286,096, which is a division of Ser. No. 771,183, Feb. 23, 1977, Pat. No. 4,155,910, which is a division of Ser. No. 555,375, Mar. 5, 1975, Pat. No. 4,039,552.

[51] Int. Cl.³ ................. C07D 235/28; C07D 263/58; C07D 285/08
[52] U.S. Cl. .................................... 548/130; 548/125; 548/132; 548/142; 548/144; 548/166; 548/186; 548/213; 548/221; 548/255; 548/265; 548/229; 548/243; 548/339; 548/329; 548/377

[58] Field of Search .............. C07D/285/12; 548/130, 548/132, 166, 221, 329, 125, 142, 144, 186, 213, 221, 255, 265, 229, 243, 339, 377

[56] References Cited

U.S. PATENT DOCUMENTS

| | | | |
|---|---|---|---|
| 3,087,932 | 4/1963 | Little et al. | 548/142 |
| 4,039,552 | 8/1977 | Brois et al. | 548/130 |
| 4,097,387 | 6/1978 | Caspari et al. | 548/142 |
| 4,155,910 | 5/1979 | Brois et al. | 548/142 |

Primary Examiner—Alton D. Rollins
Attorney, Agent, or Firm—R. A. Dexter; J. J. Mahon

[57] ABSTRACT

Azole and azoline disulfides useful as corrosion inhibitors and antiwear agents are prepared by the halogen-induced coupling of a thiol reactant e.g., hydrocarbyl mercaptans, with a metal azole thiolate, e.g. the potassium salt of 3,5-bis-mercapto 1,2,4-thiadiazole or 2,5-bis-mercapto 1,3,4 thiadiazole in a 2-phase reaction medium comprising a mixture of a hydrocarbon and water.

13 Claims, No Drawings

TWO-PHASE PROCESS FOR THE PREPARATION OF AZOLE AND AZOLINE DISULFIDES

This is a division of application Serial No. 970,230, filed Dec. 18, 1978, now U.S. Pat. No. 4,286,096, which is a division of Serial No. 771,183, filed Feb. 23, 1977, now U.S. Pat. No. 4,155,910 which is a division of Serial No. 555,375, filed Mar. 5, 1975, now U.S. Pat. No. 4,039,552.

FIELD OF THE INVENTION

This invention relates to a novel process for the preparation of hydrocarbyl dithio azoles or azolines which have use as corrosion inhibitors in lubricants.

More particularly it relates to a novel process involving the halogen-induced coupling of a thiol reactant and a metal azole thiolate in a two phase reaction medium comprising a mixture of a non-polar solvent and water.

PRIOR ART

It is well known that polysulfides which contain an N-C-S substituent as part of a heterocyclic ring system are highly effective in inhibiting the corrosion of copper and silver resulting from the presence of certain sulfur compounds in lubricating oils. A study of the use of various compounds containing the N-C-S linkage as sulfur-corrosion inhibitors was reported by R. Q. Little and R. W. Watson in a paper entitled "Inhibitors for Sulfur Corrosion of Copper and Silver" and presented at a symposium on additives in the petroleum industry before the Division of Petroleum Chemistry of the American Chemical Society at Detroit, Apr. 4-9, 1965.

U.S. Pat. No. 2,963,433 relates to the preparation of 2-(alkyl dithio) benzo-thiazoles and 2-(alkyl dithio) benzoxazoles, and their use as corrosion inhibitors. Therein, the heterocyclic compounds were made by reacting alkyl mercaptan with chlorine in an organic medium and then reacting the anhydrous alkyl sulfonyl chloride with a suspension of the sodium salt of 2-mercapto benzothiazole or the sodium salt of 2-mercapto benzoxazole in $CCl_4$ to form the corresponding 2-(alkyl dithio) benzo-thiazoles or 2-(alkyl dithio) benzoxazoles.

U.S. Pat. No. 2,963,432 is concerned with the preparation, and use in lubricant compositions of 2-(alkyl dithio) benzimidazoles. The preparation comprises reacting alkyl sulfonyl chloride with the sodium salt of 2-mercapto benzimidazole in an organic medium.

U.S. Pat. No. 2,719,126 describes 2,5-bis (hydrocarbyl dithio) 1,3,4-thiadiazoles as a useful class of corrosion inhibitors. They are prepared by either reacting 2,5-dimercapto 1,3,4 thiadiazole with a suitable sulfonyl chloride, or by first forming the disulfonyl chloride of the thiadiazole and then reacting the dry reagent with a primary or tertiary mercaptan. The use of the 1,3,4-thiadiazole system as an effective sulfur scavenger is also taught by E. K. Fields, in Industrial Engineering Chemistry, 49, 1361 (1957).

U.S. Pat. No. 3,087,932 describes the use of 3,5-bis(-hydrocarbon dithio) 1,2,4 thiadiazoles, and their preparation by reacting the 1,2,4-thiadiazole 3,5-bis sulfonyl chloride with a mercaptan is methylene chloride. These disulfides are taught to be useful as corrosion inhibitors in lubricants.

U.S. Pat. No. 3,691,183 teaches the reaction of olefins with 1,2,4-thiadiazole-3,5-yl bis sulfonyl chloride in a single phase process to provide the olefin adduct of said bis sulfonyl chloride (see also an article by W. A. Thaler and J. R. McDivitt in J.Org. Chem., Vol. 36, No. 1, pp. 14-18 (1971)).

The above-described preparations for production of mixed disulfide of thiol-substituted azoles are all (except for U.S. Pat. No. 3,087,932) believed to involve a two-stage process whereby a mercaptan or its salt is first converted to a sulfonyl chloride, and the resulting sulfonyl chloride is reacted with a thiol reactant to form the disulfide. The disadvantages of the earlier processes for making the heterocyclic disulfides are recognized in U.S. Pat. No. 3,087,932 which points out that throughout these prior art reaction processes the reaction conditions require that the reactants be kept anhydrous. However, the thiadiazole starting materials are normally made commercially as their sodium salts, which salt itself cannot be used as a starting material in the chlorination step. Thus, in many cases a 3-stage process is required, i.e., acidification of the metal salt, chlorination, and reaction with mercaptan.

In the one-step production of 2,5-bis(hydrocarbyl dithio)-1,3,4 thiadiazoles, U.S. Pat. No. 3,087,932 teaches reacting a 2,5 dimercapto 1,3,4-thiadiazole with a mercaptan and hydrogen peroxide. The reaction mixture has three phases: an organic phase comprising alkyl mercaptan; an aqueous phase containing hydrogen peroxide; and a solid phase which comprises the 2,5 dimercapto 1,3,4-thiadiazole.

The multi-step processes of the prior art are costly and time consuming. The one-step process of U.S. Pat. No. 3,087,932 necessitates the involved preparation and handling of the free mercapto thiadiazoles from the commercially available salts and the use of the hazardous hydrogen peroxide.

SUMMARY OF THE INVENTION

It has been discovered that dithio derivativer of thiol-substituted azoles and azolines can be readily prepared in excellent yields by a novel and improved process involving the halogen-induced oxidative coupling of a azole or azoline with a thiol reactant in a two-phase medium comprising a mixture of a non-polar solvent and water.

Thus, this invention describes a process wherein the halogen-induced oxidative coupling of a mercapto substituted azole or azoline or the alkali or alkaline earth metal salt thereof and a thiol reactant including a hydrocarbon-substituted thiol, thiolate, thioacid and thioate or a polysulfide is performed in a two-phase medium comprising organic solvent and water to form hydrocarbyl dithio azoles or hydrocarbyl dithio azolines.

In carrying out the process of the invention it has been found useful in the production of a novel class of compounds which can be described as bis-3,5 (N,N-dialkyl dithiocarbonyl thio) 1,2,4 thiadiazoles. This novel class of compounds wherein the alkyl group contains from 1 to 20 carbon atoms, preferably 1 to 5 carbon atoms, are useful corrosion inhibitors for lubricants.

COUPLING REACTION

The general, preferred method of making hydrocarbon dithio azoles or hydrocarbon dithio azolines in accordance with the process of the invention is to gradually charge a suitable halogen such as chlorine into a rapidly stirred mixture comprising an aqueous alkaline solution of the alkali or alkaline earth metal salt of the azole or azoline intermixed with a hydrocarbon solution of hydrocarbon mercaptan or polysulfide at a temperature in the range from 0° C. to 90° C., preferably in the range from 20° C. to 60° C. After addition of the halogen oxidant, it may be advantageous to maintain the well-stirred mixture at a temperature in the above preferred range and especially at about 40° C. for a period of from ¼ to 2 hours to assure high yield. The reaction mixture is then allowed to settle, and separate into an upper organic solvent layer containing the hydrocarbon dithio-azole or hydrocarbon dithio azoline, and a lower aqueous layer containing inorganic salt products. The upper organic solvent layer is removed from the mixture, washed with e.g. 10% aqueous sodium carbonate solution, dried over anhydrous $Na_2CO_3$ powder, and the solvent stripped to obtain the desired product.

Usually the product comprises the hydrocarbon dithioazoles or azolines, although the use of $S_xCl_2$ coupling agents (where x=1–4) may, depending on reaction conditions, result in higher polysulfide derivatives such as the tri- and tetra-sulfides.

The selectivity of the process is striking, for with high yields of the desired product, the pure mixed disulfides are essentially free of the symmetrical alkyl disulfides, which depending on reaction conditions may form as intermediates but quickly collapse to product upon further chlorinolysis.

The reaction appears to proceed across the phase boundaries so as to selectively couple the reactants of the separate phases. This phenomenon is not fully understood, and the results are most surprising in the light of the prior art and the assertion in U.S. Pat. No. 3,087,932 that the coupling reaction has to be carried out under anhydrous conditions. In the suspected that halonium-type oxidants interact with azole thiolates, thiols or disulfides to engender the corresponding sulfonyl halide reactants which inter alia, interact selectively with free mercaptan or thiolate or disulfide reactants to give high yields of mixed disulfide product. Moreover, the presence of hydrocarbon or halohydrocarbon solvent is essential in the process of the invention to realize high yields of product. Without solvent, competitive hydrolysis and sulfur extrusion reactions tend to decrease the yield of the desired product. It is not known with certainty what role the organic phase plays in improving product yields; however, it is suspected that the water sensitive intermediates and products rapidly transfer to the organic phase and maintain their integrity for a time sufficient for further reaction or until isolation, respectively. Moreover, product isolation using the two-phase process is greatly facilitated. Thus in one embodiment the claimed invention is to a process of preparing a disulfide of a thiol-substituted azole comprising the step of halogen-induced oxidative coupling of said azole with a thiol reactant in a medium comprising an organic solvent phase and an aqueous phase, wherein said coupling is carried out at a temperature ranging from about 0° to about 90° C. and wherein each thiol group of an azole salt is reacted with about 0.9 to about 1.1 moles of alkane thiol or thiolate reagent using about 0.9 to about 1.1 moles of chlorine gas.

THE THIOL SUBSTITUTED-AZOLE AND AZOLINE REACTANTS

In general, the heterocyclic pentatomic ring compounds useful as starting materials in the process of the invention are mercapto substituted azoles and azolines. Representative azoles include oxadiazoles, isoxazoles, isothiazoles, oxazoles, diazoles, triazoles, thiazoles, imidazoles, benzoxazoles, benzimidazoles, etc. Representative azolines include thiazolines, oxazolines, imidazolines, etc.

Thus, the starting materials include 2-mercaptothiazole, 2-mercapto-oxazole, 2-mercapto-imidazole, 2-mercapto-thiazoline, 2-mercapto-oxazoline, or 2-mercapto-imidazoline. Other suitable heterocyclic reactant include 2-mercapto-benzo-thiazole, 2-mercapto-benzoxazole or 2-mercapto-benzimidazole. Preferred reactants are 2,5 dimercapto 1,3,4-thiadiazole or 3,5-dimercapto 1,2,4 thiadiazole.

In the preferred reaction procedure, the starting materials comprise the alkali or alkaline earth metal thiolate salts of the azoles or azolines, rather than the free mercapto-azoles or azolines. This is because of their solubility in water; moreover, the preferred mercapto-substituted azoles or azolines are conveniently manufactured as their alkali or alkalines earth metal salts. It is, however, within the scope of the present invention to use instead the alkali or alkaline earth metal salts of the hydrocarbon thiols and reset them in the mixed aqueous/organic solvent system with the mercapto-substituted azoles or azolines.

One may also use as the starting materials the alkali or alkaline earth metal salts of the mercapto-substituted azoles and azolines and the alkali or alkaline earth metal salts of the hydrocarbon substituted thiols or thio acids (the thioates) in the aqueous/organic solvent mixture. Alternatively, the azoles or azolines and the hydrocarbon substituted thiols may be charged to the aqueous organic solvent system and the metal salts formed in situ by addition of a suitable alkali or alkaline earth metal base. Thus, this claimed invention can be expressed as a process of preparing a disulfide of a thiol-substituted azole comprising the step of halogen-induced oxidative coupling of a metal salt of said azole with an alkane thiol or thiolate in a medium comprising an organic solvent phase and an aqueous phase containing a volume ratio of solvent hydrocarbon to water of at least about 0.1, and said salt of said azole is of the class consisting of alkali metals and alkaline earth metals and present in an amount ranging from about 10% by weight of the aqueous phase to saturation of said aqueous phase.

THIOL REACTANT

In the process of this invention the hydrocarbon thiol reactant used as a starting material may be any hydrocarbon containing between 2 and 100 carbon atoms with an attached thiol or alkali or alkaline earth metal thiolate group. Suitable thiols include but are not limited to n-butyl mercaptan, isobutyl mercaptan, t-butyl mercaptan, hexyl mercaptans, octyl mercaptans, diisobutenyl mercaptan, docyl mercaptans, dodecyl mercaptans, cetyl mercaptans, cyclohexyl mercaptan, benzyl mercaptan, thiophenol and longer chain alkyl mercaptans derived from propane polymers and isobutylene polymers. It is understood that the above thiols may also be used as their alkali or alkaline earth metal salts, i.e. thiolates.

In one embodiment of this invention the thiol reactant is an alkane thiol and more particularly said alkane thiol contains from about 4 to about 50 carbons.

Other suitable reactants include mono-thio acids and dithio acids such as thioacetic, thiobenzoic, dithioacetic, dithiopropionic, and dithiobenzoic acid; useful thiophosphoric and esters include dialkyl dithiophosphoric and diaryl dithiophosphoric acid. The corresponding salts of the above acids, i.e. thioates are equally useful.

Other suitable reactants containing a metal thiolate group are dithiocarbamates such as sodium diethyl dithiocarbamate, sodium dibutyl dithiocarbamate; xanthates such as sodium ethyl xanthate and sodium butyl xanthate; trithiocarbonates, such as sodium t-butyl trithiocarbonate and sodium t-octyl trithiocarbonate.

In another embodiment of the present invention, di- and polysulfides can also function as reactants. The di- and polysulfides behave in the same manner as the mercaptan reactants. Examples of such polysulfides are t-butyl disulfide, t-octyl disulfide, t-dodecyl disulfide, t-octyl tetrasulfide, t-nonyl tetrasulfide, and t-dodecyl tetrasulfide. Other disulfides including diethyl thiuram disulfide, 2-benzothiazolyl disulfide, tetramethylthiuram disulfide and tetraethylthiuram disulfide, are also useful.

In another embodiment of this invention, the thiol reactant may be replaced by an olefin when $S_xCl_2$ reagents are employed. Useful olefins for this especial embodiment include isobutylene, 1-butene, 2-butene, 2-methyl-1-butene, 2-methyl-2-butene, pentenes, hexenes, octenes, decenes, styrenes, cyclohexene, cyclic terpenes such as $\alpha$pinene, $\beta$-pinene, etc., and longer chain alkenes derived from propene, and isobutylene polymers having six to about 64 propene or isobutylene units per molecule. In this halogen-induced coupling reaction the mercapto azoles and azolines are presumably converted to transient thiosulfenyl chloride intermediates which rapidly add to an olefin such as diisobutylene to give the hydrocarbyldithio azole and azoline products and, under suitable reaction conditions, higher sulfur analogs.

OXIDATIVE COUPLING REAGENTS

In general, any reagent which can generate a halonium ion is effective for coupling the reactants. Illustrative of suitable halonium-type reagents are chlorine, bromine, hypochlorites (such as LiOCl, NaOCl, Ca(OCl)$_2$, t-butyl hypochlorites, etc.), sulfuryl chloride, and sulfur chlorides $S_xCl_2$ where $x=1-4$. Depending on reaction conditions, the $S_xCl_2$ coupling reagents may give higher sulfide derivatives e.g. tri- and tetrasulfides.

ORGANIC PHASE

The presence of an organic solvent is an essential feature of the process of the invention in achieving high yields of product. By organic solvent is meant a hydrocarbon or halohydrocarbon. It is desirable to have at least 10% of organic solvent present in the process based upon the amount of water present, but usually equal volumes of water and solvent give good results. As the volume percent of hydrocarbon diluent approaches zero, the alleged side reactions intervene and product quality and yield decline. Higher proportions of organic solvent are employable if economically feasible. Examples of suitable solvents are pentane, hexane, heptane, cyclohexane, methylene, chloride, chloroform, carbon tetrachloride, trichlorethylene, tetrachlorethylene, benzene, toluene and chlorobenzene. In a limited embodiment of this invention, said organic solvent is a member of the class of hydrocarbons consisting of pentane, hexane, heptane, octane, a neutral oil, methylene chloride, chloroform, carbon tetrachloride and trichloroethylene.

AQUEOUS PHASE

Usually sufficient water is employed to solubilize the metal salt of the mercapto azole or azoline, alkali (if present) and by-product salts formed during the oxidative coupling with halogen. Normally concentrated (e.g. 25–50%) aqueous solutions of metal salts of the mercapto azole or azoline are employed, although more dilute solutions are also operative. Should salts separate from solution during the coupling reaction, sufficient water may be added to dissolve them, and the avoidance of solid materials during product isolation results in better phase separation. In one embodiment of this invention the hydrocarbon to water volume ratio is from about 0.1 to about 10, preferably 1 to about 3.

Some product degradation can occur if halogen acid formed during oxidative coupling with halogen is not scavenged. In a preferred embodiment of the invention the aqueous phase is basified as the halogen is added with sufficient alkali to neutralize completely the halogen acid generated. However, sufficient base to fully neutralize halogen acid may be conveniently added prior to the chlorine-induced coupling reaction. When sufficient base is not added prior to or during the reaction, the halogen acid formed during coupling may be neutralized by adding sufficient base after the oxidative coupling is complete. In one embodiment of the invention there is added during the reaction from about 1 to about 2 mole of equivalents of base whereby the pH of the aqueous phase is maintained at about 7.

STOICHIOMETRY

The theoretical amounts of reactant required in the process are 1 mole of halogen and 1 mole thiol reactant, e.g. mercaptan, for each mercaptan group present in the azole or azoline nucleus. In carrying out the process of the invention, a range of from about 0.9 to about 1.1 moles of thiol reactant per mercaptan group present on the thiazole or thiazoline ring can be used. In the case of the bis-mercapto thiadiazoles, the theoretical amounts of reactants are 2 moles of chlorine and 2 moles of thiol reactant, for each mole of thiadiazole. It is preferred that about 1.9–2.1 moles of thiol reactant per mole of dimercapto thiadiazole be used. In some cases a slight excess of the theoretical amount (e.g. 10% excess) of halogen is preferred.

The following examples illustrate the direct or one-step synthesis of dithio derivatives of thiol-substituted azoles via the halogen induced oxidative coupling of a thiol-substituted azole in aqueous solution with thiol reactant dissolved in the organic phase. The halogen oxidants employed were: (i) hypochlorite salts, (ii) chlorine, (iii) bromine, (iv) sulfur chlorides and (v) sulfuryl chloride. In most instances, the organic solvents employed were benzene and methylene chloride.

Examples 1 and 2 describe the preparation of 3,5 bis-(hydrocarbyl dithio) 1,2,4 thiodiazoles using a hypochlorite salt as halogen oxidative coupling agent.

EXAMPLE 1

One mole (84 g of 50% aqueous solution) of cyanamide was combined with 600 ml of water and 95 g (1.25 moles) of carbon disulfide in a reactor blanketed with nitrogen at ambient temperature. To the stirred mixture was added dropwise a 50% aqueous solution of potassium hydroxide (224 g of 50% aqueous KOH). After base addition ($\frac{1}{2}$ hour), a mole (32 g) of sulfur was charged into the reactor. The mixture was stirred at room temperature overnight and then refluxed one hour at 50° C. Filtration of the mixture afforded 7 g of sulfur, indicating that 0.76 mole of bis-potassium salt of 3,5 dimercapto 1,2,4 thiadiazole had formed. To the aqueous solution of salt was then added an equal value of pentane containing 1.52 moles (222 g) of t-octyl mercaptan. The two-phase mixture was stirred at room temperature and 400 g of lithium hypochlorite slurried in 500 ml. of water were added gradually. External cooling was applied to keep the temperature at about 40°–45° C. After LiOCl addition, the reaction mixture was stirred at 40°–45° C. for two hours and at room temperature overnight. The pentane layer was separated off, dried over $Na_2CO_3$ and concentrated by rotoevaporation. The crude product (107 g) showed an infrared spectrum similar to that for 3,5-bis(t-octyldithio) 1,2,4 thiadiazole.

EXAMPLE 2

Into a two liter round bottom flask equipped with dropping funnel, thermometer, reflux condenser and stirrer was aded a quarter mole (36.6 g in 119 g aqueous solution) of bis-potassium perthiocyanate salt, 300 ml. of water, a half mole (101 g) of t-dodecyl mercaptan and 300 ml of hexane. To this stirred mixture was added, in 10 g portions, 120 g solid calcium hypochlorite over an hour period. The reaction temperature steadily rose and after final addition reached 47° C. After stirring the mixture overnight at room temperature, a second charge (130 g) of $Ca(OCl)_2$ was added as before. After addition, the mixture was stirred at ambient temperature overnight and then filtered. The hexane phase was separated from the filtrate, dried over $Na_2CO_3$ and rotoevaporated at 80°–90° C. for two hours. The residue weighed 87 g. Infrared and elemental analyses indicated that the product contained 65% active ingredient of 3,5-bis(t-dodecyldithio) 1,2,4 thiadiazole.

The following Examples 3–22 illustrate the preparation of 3,5 bis-(hydrocarbyl dithio) 1,2,4 thiadiazoles using chlorine as the oxidative coupling reagent in a hydrocarbon/water and halocarbon/water system.

EXAMPLE 3

A quarter mole of the bis-potassium salt of 3,5 dimercapto 1,2,4 thiadiazole was basified with a half mole (32 g. of 85% KOH) of potassium dissolved in 100 ml. water. After adding 73 g (0.5 mole) of t-octyl mercaptan (in 600 ml. of hexane) to the aqueous alkaline solution, chlorine gas (35.5 g) was bubbled into the rapidly stirred solution. The reaction temperature was maintained below 30° C. with external cooling. In the course of reaction, the mixture featured a series of color changes ranging initially from a deep red to orange and eventually become light yellow. After stirring at ambient temperature for an hour, the hexane layer was separated from the reaction mixture, washed with a half liter of 10% aqueous $Na_2CO_3$ solution, and filtered through a cake of celite intermixed with $Na_2CO_3$. The filtrate, after being rotoevaporated for one hour at 60° C., afforded a residue which weighed 84 g and featured an infrared spectrum consistent with that for 3,5 bis(t-octyldithio) 1,2,4 thiadiazole. The residue analyzed for 51.26% carbon, 8.36% hydrogen, 4.43% nitrogen, 37.1% sulfur and 0.36% chlorine.

EXAMPLES 4–11

In the manner described in Example 3, several reaction parameters were varied to illustrate the versatility of the two-phase system in achieving high yields of 3,5 bis-(octyl dithio)-1,2,4-thiadiazole. The examples reveal that alkali and alkaline earth metal salts of 3,5-dimercapto-1,2,4-thiadiazole can be oxidatively coupled to t-octyl mercaptan by chlorine gas in a number of organic solvents in contact with a basic or neutral aqueous medium. Yield data for 3,5 bis-(t-octyldithio)-1,2,4-thiadiazole prepared with various salts using different organic phases in contact with basic or neutral aqueous media are shown in Table 1. Oxidative coupling was effected at about 40° C. by bubbling two mole equivalents of chlorine into equal volumes of organic diluent containing t-octyl mercaptan (two mole equivalents) and an aqueous medium containing the salt of 3,5 dimercapto-1,2,4-thiadiazole (one mole equivalent) and two mole equivalents of potassium hydroxide if base is used. After reaction, the isolated organic phase was washed with a 10% aqueous $Na_2CO_3$ solution, dried over $Na_2CO_3$, filtered and rotoevaporated.

TABLE 1

YIELD DATA FOR 3,5 BIS-(t-OCTYLDITHIO-1,2,4-THIADIAZOLE

| Examples | Salt* | Solvent System[a] | % Yield [c] |
|---|---|---|---|
| 4 | K | Hexane | 78 |
| 5 | K | Ag.Alkali[b] Hexane | 80 |
| 6 | Ca | Ag.Alkali Hexane | 100 |
| 7 | K | Ag.Alkali Hexane | 73 |
| 8 | Ca | Water[d] Hexane | 81 |
| 9 | K | Water $CH_2Cl_2$ | 75 |
| 10 | Ca | Water $CH_2Cl_2$ | 62 |
| 11 | K | Water Benzene | 60 |
|  |  | Water |  |

*metal salt of 3,5 dimercapto-1,2,4-thiadiazole
[a]About equal volumes of organic solvent and water were used.
[b]Basified with two mole equivalents of potassium hydroxide.
[c]Based on salt of 3.5 dimercapto 1,2,4 thiadiazole
[d]Water is strongly acidic after complete reaction.

EXAMPLE 12

A quarter mole of bis-potassium salt of 3,5 dimercapto 1,2,4-thiadiazole was combined with 1 mole of KOH (132 g of a 50% aqueous KOH solution). Thus, a half mole (101 g) of t-dodecyl mercaptan dissolved in 600 ml. of hexane was added to the aqueous phase. The well-stirred mixture was treated with a half mole (35.5 g) of chlorine by bubbling $Cl_2$ gas into the mixture at about room temperature. External cooling was needed to maintain the temperature at about 20° C. After addition, the mixture was stirred for ½ hour. Analysis of the mixture by infrared showed that the oxidative coupling reaction was incomplete, so an additional 10 g of chlorine was bubbled into the stirred mixture at about 25° C.: after stirring for an hour at room temperature, the hexane layer was separated from the mixture, washed with 10% aqueous alkali, dried over $Na_2CO_3$ and rotoevaporated at 60° C. for an hour. The infrared spectrum of the crude product (128 g) was consistent with the 3,5 bis-(t-dodecyldithio) 1,2,4-thiadiazole structure.

EXAMPLES 13–16

In the manner described in Example 12, several reaction parameters were varied to demonstrate the flexibility of the two-phase system in obtaining high yields of 1,2,4-thiadiazole disulfides. Yield data for 3,5 bis(t-dodecyldithio) 1,2,4-thiadiazole prepared in different ways are illustrated in Table 2.

TABLE 2

YIELD DATA FOR 3,5 BIS-(t-DODECYL DITHIO) 1,2,4-THIADIAZOLE

| Example | Salt* | Solvent System | Yield, % |
|---|---|---|---|
| 13 | K | Hexane | 82.5 |
| 15 | Ca | Ag.Alkali[a] Hexane | 87.3 |
| 14 | K | Ag.Alkali[b] Hexane | 91.5 |
| 16 | Ca | Water Hexane | 86.5 |
|  |  | Water |  |

*metal salt of 3,5 dimercapto-1,2,4-thiadiazole
[a] 2 mole equivalents of KOH added
[b] 3 mole equivalents of KOH added

EXAMPLE 17

In the same manner depicted in Example 12, several mercaptans were oxidatively coupled with a salt of 3,5 dimercapto-1,2,4-thiadiazole using chlorine as the halogen coupling reagent. Yield data for the 3,5 bis-(hydrocarbyl dithio)-1,2,4-thiadiazoles derived from t-butyl mercaptan n-octyl mercaptan, t-nonyl mercaptan and benzyl mercaptan are shown in Table 3.

TABLE 3

YIELD DATA FOR 3,5 BIS-(HYDROCARBYLTHIO)-1,2,4-THIADIZOLES[a]

| Example No. | Salt | Mercaptan | Solvent System | Yield* (%) |
|---|---|---|---|---|
| 17 | Ca | t-butyl | Hexane | 73 |
| 18 | K | t-butyl | Water Hexane | 85.8 |
| 19 | K | n-octyl | Ag.Alkali[b] Hexane | 73.0 |
| 20 | K | t-nonyl | Aq.alkali Hexane | 74 |
| 21 | Ca | t-nonyl | Aq.Alkali Hexane | 64 |
| 22 | K | Benzyl | Water Hexane Aq.Alkali | — |

*based on salt of 3,5 dimercapto-1,2,4-thiadiazole
[a] Coupling reaction at 30–40° C.
[b] Four mole equivalents of KOH added.

Metal thiolates as exemplified by sodium diethyl dithiocarbamate can also be coupled to 3,5-dimercapto-1,2,4-thiadiazole salts via halogen oxidative coupling as shown hereafter.

EXAMPLE 23

A quarter mole of bis-potassium salt of 3,5-dimercapto-1,2,thiadiazole and a half mole (113 g) of sodium diethyldithiocarbamate were dissolved in 400 ml of water, and combined with an equal volume of methylene chloride (400 ml.). The well stirred mixture was treated with a half mole (36 g) of chlorine by bubbling the gas into the reactor which was kept at 30° C. with external cooling. After stirring the mixture for a half hour at ambient temperature, the methylene chloride layer was isolated, dried over $Na_2CO_3$, filtered and rotoevaporated at 50° C. for about 2 hours. The filtered concentrate weighed 93 grams and analyzed for 30.70% carbon, 4.55% hydrogen, 10.95% nitrogen, and 44.80% sulfur which values are consistent with the structure of bis-3,5-(N,N-diethyl) dithiocarbamylthio-1,2,4-thiadiazole.

The following examples illustrate the suitability of bromine, sulfur chloride, and sulfuryl chloride as convenient and effective oxidants.

EXAMPLE 24

A quarter mole of the bis-potassium salt of 3,5 dimercapto-1,2,4-thiadiazole and 0.75 mole of potassium hydroxide (as a 50% aqueous solution) were dissolved in 400 ml of water. A half liter of hexane containing a half mole of t-dodecyl mercaptan was added to the aqueous solution. The mixture was oxidized with bromine by adding 84 grams of liquid $Br_2$ (over a half hour period) to the well-stirred solution kept at 30°–35° C. by external cooling. The mixture was stirred at ambient temperature for an hour. The hexane phase was separated from the mixture, dried over $Na_2CO_3$, filtered and rotoevaporated. The concentrate was refiltered, and weighed (126 grams). The infrared spectrum of the crude product was consistent with the 3,5 bis-(t-dodoevidithio)-1,2,4-thiadiazole structure and upon analysis gave 58.66% carbon, 9.51% hydrogen, 2.71% nitrogen and 22.8% sulfur.

EXAMPLE 25

A half mole of bis-potassium salt of 3,5 dimercapto-1,2,4-thiadiazole and 3 mole equivalent of KOH (as a 50% aqueous solution) were dissolved in a half liter of water and combined with about 600 ml. of hexane containing 1 mole of t-dodecyl mercaptan. The well-stirred mixture (kept at 30°–35° C.) was treated with sulfur dichloride by adding 1.5 moles of the neat $SCl_2$ reagent dropwise. After addition, the mixture was stirred at ambient temperature overnight. The hexane solution was filtered to remove sulfur, dried over $Na_2CO_3$, refiltered and rotoevaporated at 90° C. for two hours. The concentrate (228 g) analyzed for 57.72% carbon, 9.6% hydrogen, 1.60% nitrogen and 27.6% sulfur.

EXAMPLE 26

A quarter mole of the bis-potassium salt of 3,5 dimercapto 1,2,4-thiadiazole and a half mole of KOH (as a 50% aqueous solution) were diluted in 400 ml of water and combined with a half liter of hexane containing 101 g (0.5 mole) of g-dodecyl mercaptan. While stirring the mixture at room temperature, 67 g (0.5 mole) of neat sulfuryl chloride were added dropwise. The reaction temperature was kept at 30° C. with external cooling.

The $SO_2Cl_2$ addition produced a deep red emulsion which gradually lightened to a pale yellow color after 15 minutes. Following $SO_2Cl_2$ addition (15–20 minutes), the mixture was allowed to stir at ambient temperature for a half hour. Infrared analysis of the hexane layer showed unreacted mercaptan, so 3 additional grams of $SO_2Cl_2$ were added. After stirring the mixture for another half hour, the hexane layer was separated, dried and filtered. The concentrated product weighed 116 grams, and analyzed for 58.55% carbon, 9.71% hydrogen, 3.86% nitrogen and 25.9% sulfur.

In the following examples, the mercaptan reactant is replaced by an olefin and sulfur dichloride. The sulfur dichloride apparently reacts with the metal salt of 3,5 dimercapto 1,2,4 thiadiazole to generate a transient bis-thiosulfonyl chloride of perthiocyanic acid which adds rapidly to an olefin acceptor such as diisobutylene-2. The intermediary product undergoes spontaneous NCl loss to form a 3,5 bis-(alkenyl dithio) 1,2,4 thiadiazole.

EXAMPLE 27

Two tenths mole of bis-potassium salt of 3,5-dimercapto 1,2,4-thiadiazole in 200 ml water and 300 ml of methylene chloride containing a half mole (56 g) of 2,4,4-trimethyl-2-pentene were charged into a reactor and stirred at room temperature. Four tenths mole (40.9 g) of neat $SCl_2$ were added dropwise to the stirred reaction mixture which was kept at 30°–35° C. with external cooling. After addition (about one hour), the mixture was stirred at ambient temperature for one hour. Since some sulfur formed, the mixture was filtered and the methylene chloride layer was isolated, dried over $Na_2CO_3$ and refiltered. Rotoevaporation of the filtrate afforded a concentrate which weighed 49 g. Infrared analysis showed strong absorption bands at 7.82, 8.40, 9.52 and 11.13 microns. These spectral features are consistent with the proposed 3,5 bis-(alkenyl-dithio) 1,2,4 thiadiazole structure. The crude product analyzed for 46.02% carbon, 6.68% hydrogen, 5.10% nitrogen and 39.6% sulfur.

EXAMPLE 28

A quarter mole (47 g) of the calcium salt of 3,5 dimercapto 1,2,4 thiadiazole was slurried in 200 ml of $CH_2Cl_2$ containing 84 g (0.75 mole) of 2,4,4-trimethyl-2-pentene. The dropwise addition of 51.5 g (0.5 mole) of neat $SCl_2$ to the stirred mixture produced an exothermic reaction which was controlled by external cooling. Reaction temperature was maintained at about 25° C. After addition, the mixture was stirred at ambient temperature and then filtered. Rotoevaporation gave 87 grams of an oil which featured an infrared spectrum with prominent absorption bands at 7.0, 8.33, 9.47, and 11.1 microns. The product analyzed for 50.08% carbon, 7.32% hydrogen, 3.84% nitrogen, and 33.0% sulfur.

EXAMPLE 29

Two tenths mole (20.6 g) of neat sulfur dichloride were added dropwise to 0.1 mole (18.8 g) of the calcium salt of 3,5 dimercapto 1,2,4 thiadiazole slurried in 200 ml of $CH_2Cl_2$. The temperature of the stirred reaction mixture gradually climbed to about 30° C. right after $SCl_2$ addition. The reddish $CH_2Cl_2$ solution gradually turned yellow after stirring at ambient temperature for 15 minutes. The resulting yellow slurry was then added to 0.2 mole (23 g) of 2,4,4-trimethyl-2-pentene in 200 ml. of $CH_2Cl_2$ at about 25° C. The addition produced an exothermic reaction with the evolution of hydrogen chloride. Cooling was applied to keep the temperature below 35° C. After being stirred at ambient temperature for an hour, the reaction mixture was filtered. Rotoevaporation afforded 35 grams of crude product which featured an IR spectrum with absorption bands at 7.0, 8.3, 9.6 and 11.1 microns. The product analyzed for 50.80% carbon, 7.45% hydrogen, 4.01% nitrogen, and 33.0% sulfur.

EXAMPLE 30

0.05 mole (11.3 g) of the potassium salt of 2,5 dimercapto 1,3,4 thiadiazole was dissolved in 100 ml. water. After adding 0.1 mole (14.6 g) of t-octyl mercaptan (in 300 ml. of hexane) to the aqueous solution, 0.1 moles of chlorine gas (7.1 g.) was bubbled into the rapidly stirred mixture. The reaction temperature was maintained below 30° C. with external cooling. After stirring an ambient temperature for an hour, the hexane layer was separated from the reaction mixture, wshed with a half liter of 10% aqueous $Na_2CO_3$ solution, and filtered through a cake of celite intermixed with $Na_2CO_3$. The filtrate, after being rotoevaporated for one hour at 60° C., afforded a residue which weighed 14 g and featured an infrared spectrum consistent with that for 2,5 bis-(t-octyl dithio) 1,3,4 thiadiazole. The residue analyzed for 48.77 wt. % carbon, 7.62 wt. % hydrogen, 5.91 wt. % nitrogen, 35.8 wt. % sulfur and 0.69 wt. % chlorine.

EXAMPLE 31

A half mole (20.0 g) of sodium hydroxide was dissolved in 500 ml. of water. After allowing the solution of sodium hydroxide to cool to room temperature, 0.5 mole (83.5 g) of 2-mercaptobenzothiazole was slowly stirred in, resulting in a clear yellow solution. To this solution was added 750 ml of heptane and 0.5 mole (101.0 g) of t-dodecyl mercaptan.

The mixture was thereafter stirred at room temperature while about a half mole (36 g) of chlorine was passed into it at a rate of 100 cc/min. over a 1½ hour period. During chlorination, the temperature of the mixture increased from 23° C. to 44° C. The small amount of solid (6.1 g) that formed was removed by filtration. The heptane layer was then separated off and passed through a bed of anhydrous sodium carbonate to remove any last traces of water. The heptane solution was then stripped on a rotoevaporator to yield 178 gm. (97%) of the expected product which featured an infrared spectrum identical with that for authentic 2-(t-dodecyldithio) benzothiazole. High yields (>90%) of 2-(t-dodecyldithio) benzoxazole and 2-(t-dodecyldithio)benzimidazole were also obtained from the corresponding azole thiols using the method of Example 31.

The following examples are illustrative of the advantages of the process of the invention.

EXAMPLE 32

In this example the procedure of Example 3 was followed except that the 0.5 mole of t-octyl mercaptan was not dissolved in hexane but directly stirred into the reaction mixture. No hexane was present during the reaction. At the end of the reaction time of about ½ hour, a soapy yellow emulsion had been obtained, and upon standing for about ½ hour no separation of the liquid emulsion phase occurred although a mass of gummy sulfur deposited on the bottom of the reaction vessel. Thereafter, 600 ml of hexane was added to facilitate separation. After stirring about 1 hour the hexane layer was separated from the mixture, washed with a 10% aqueous alkali and dried over $Na_2CO_3$. The infrared spectrum of the hexane showed a response not consistent with the presence of 3,5-bis-(t-octyldithio)-1,2,4-thiadiazole structure which was obtained in substantial yield when the process of Example 3 was followed.

EXAMPLE 33

The procedure of Example 30 was followed except that the 300 ml of hexane was replaced by 100 ml of water. No hexane was present during the reaction. Addition of the chlorine produced a soapy, yellow-like product which tended to separate out. The reactant mixture was stirred for ½ hour at a temperature below 30° C. after completion of the addition of the chlorine. Thereafter 300 ml of hexane was added to facilitate extraction of the prospective product from the reaction mixture. The infra-red spectrum obtained from a portion of the recovered hexane showed a minor absorption which could be consistent with 2,5-bis-(t-octyldithio) 1,3,4-thiadiazole, however, no appreciable product was formed. The yellow substance which had been produced became granulated and gave the appearance of sulfur. This yellow material weighed about 5 grams.

EXAMPLE 34

The procedure of Example 33 was followed except that 0.1 moles (5.6 g) of KOH was added to the salt solution of the 2,5 dimercapto 1,3,4 thiadiazole and no hexane was added at any time to the reaction mixture. The IR absorption curve obtained from a sample of the non-aqueous layer showed no absorption which would be consistent with 2,5-bis-(t-octyl-dithio) 1,3,4 thiadiazole. After the reaction mixture stood at ambient temperature for about 12 hours, about 200 ml. of hexane was added and the mixture then stirred for one-half hour. After separation, a sample gave an IR absorption curve identical with that shown by sample taken about 12.5 hours before.

As previously indicated, the compounds of this invention are useful as corrosion inhibitors particularly for brass in lubricants. They can be employed in a variety of lubricating compositions based on diverse oils of lubricating viscosity, including natural and synthetic lubricating oils and mixtures thereof. The lubricating compositions contemplated include principally crankcase lubricating oils for spark-ignited and compression-ignited internal combustion engines including automobile and truck engines, two-cycle engine lubricants, aviation piston engines, marine and railroad diesel engines and the like. However, automatic transmission fluids transaxle lubricants, gear lubricants, metal-working lubricants, hydraulic fluids and other lubricating oil and grease compositions can benefit from the incorporation of the present compounds.

It is to be understood that the examples present in the foregoing specification are merely illustrative of this invention and are not intended to limit it in any manner; nor is the invention to be limited by any theory regarding its operability. The scope of the invention is to be determined by the appended claims.

What is claimed is:

1. A process for preparing a polysulfide of a thiol-substituted azole or azoline comprising the step of halogen-induced oxidative coupling of a 2-mercapto azole or azoline or the alkali or alkaline earth metal salt thereof with a hydrocarbon substituted $C_2$-$C_{100}$ polysulfide reactant in a two-phase liquid reaction medium comprising a non-polar organic solvent phase and an aqueous phase.

2. A process of claim 1 wherein said polysulfide is a dialkyl disulfide of the class consisting of t-butyl disulfide, t-octyl disulfide and t-dodecyl disulfide.

3. The process of claim 1 wherein said polysulfide is a member of the class consisting of t-octyl tetrasulfide, t-nonyl tetrasulfide and t-dodecyl tetrasulfide.

4. The process of claim 1 wherein said polysulfide is a member of the class consisting of diethyl thiuram disulfide, 2-benzothiazolyl disulfide, tetramethylthiuram disulfide and tetraethylthiuram disulfide.

5. The process of claim 1 wherein said coupling is carried out at a temperature ranging from about 0° to about 90° C.

6. The process of claim 1 wherein the salt of said azole is of the class consisting of alkali metals and alkaline earth metals and is present in an amount ranging from about 10% by weight of the weight of the aqueous phase to saturation of said aqueous phase.

7. The process of claim 1 wherein the oxidative coupling reagent consists of the class of chlorine, bromine, t-butyl hypochlorite, sulfuryl chloride, sulfur chloride and metal hypochlorite salts.

8. The process of claim 1 wherein said organic solvent is a member of the class of hydrocarbons consisting of pentane, hexane, heptane, octane, a neutral oil, methylene chloride, chloroform, carbon tetrachloride, and trichloroethylene.

9. The process of claim 2 wherein said azole is a 3,5-bis-mercapto-1,2,4-thiadiazole.

10. The process of claim 2 wherein said azole is 2,5-bis-mercapto-1,3,4-thiadiazole.

11. The process of claim 1 wherein said thiol-substituted azole is 2-mercapto-benzoxazole.

12. The process of claim 1 wherein said thiol-substituted azole is 2-mercapto-benzimidazole.

13. The process of claim 1 wherein said thiol-substituted azole is 2-mercapto-benzothiazole.

* * * * *